United States Patent [19]

Bhat et al.

[11] Patent Number: 5,417,972
[45] Date of Patent: May 23, 1995

[54] METHOD OF KILLING B-CELLS IN A COMPLEMENT INDEPENDENT AND AN ADCC INDEPENDENT MANNER USING ANTIBODIES WHICH SPECIFICALLY BIND CDIM

[75] Inventors: Neelima M. Bhat, Cupertino; Marcia M. Bieber, Los Altos; Nelson N. H. Teng, Hillsborough, all of Calif.

[73] Assignee: The Board of Trustees of the Leland Stanford Junior University, Stanford, Calif.

[21] Appl. No.: 101,436

[22] Filed: Aug. 2, 1993

[51] Int. Cl.⁶ .......................................... A61K 39/395
[52] U.S. Cl. ................ 424/137.1; 424/140.1; 424/142.1; 424/152.1; 424/141.1; 424/156.1; 424/174.1; 435/240.1
[58] Field of Search ...................... 530/388.15, 388.73, 530/413; 424/85.8, 137.1, 140.1, 142.1, 152.1, 156.1, 141.1, 174.1; 435/70.21, 172.2, 240.27, 240.1

[56] References Cited

PUBLICATIONS

Grillot–Courvalin, Catherine et al., "An anti–B cell autoantibody from Wiskott–Aldrich syndrome which recognizes i blood group specificity on normal human B cells," Eur. J. Immunol. (1992) 22:1781–88.
Teng et al., PNAS, 82:1790, 1985.
Bhat et al., J. Immunol., 151:5011, 1993.
Osband et al., Immunol. Today, 11:193, 1990.
Harris et al., Tibtech, 11:42, 1993.

*Primary Examiner*—David L. Lacey
*Assistant Examiner*—F. Christopher Eisenschenk
*Attorney, Agent, or Firm*—Cooley Godward Castro Huddleson & Tatum

[57] ABSTRACT

Methods are provided for inducing cell death in B-cells, including neoplastic B-cells, by employing reagents that bind to a B-cell epitope. Particularly, antibodies specific for the marker can be administered to a host to induce death in B-cells to which the antibodies bind or can be used in ex vivo clinical situations to selectively remove B-cells. A B-cell specific oligosaccharide epitope useful as a B-cell marker has been identified. The ligand being recognized on B lymphocytes has no apparent similarities to any of the known pan-B cells markers. In addition, proteins which specifically bind the disclosed epitope are provided. Human monoclonal antibody 216, which recognizes this B-cell epitope, is cytotoxic to B-cells and binds all CD19+ and CD20+ B lymphocytes in human peripheral blood and spleen. Furthermore, MAb 216 does not distinguish B cells by the isotype expressed, binding IgG+ and IgM+ cells with equal intensity, and also bind all B cells regardless of their CD5 expression. Methods to inhibit neoplastic B-cell growth by administering a B-cell-cytotoxic protein are presented. These products and methods find use in diagnosis and therapy.

7 Claims, No Drawings

METHOD OF KILLING B-CELLS IN A COMPLEMENT INDEPENDENT AND AN ADCC INDEPENDENT MANNER USING ANTIBODIES WHICH SPECIFICALLY BIND CDIM

TECHNICAL FIELD

The field of this invention is the control of B-cell proliferation in a mammalian host as a therapy.

BACKGROUND

The immune system is the first line of defense against many pathologies. Particularly, the lymphoid compartment is concerned with monitoring tumorigenesis, invasion by pathogens, such as bacteria and viruses, aiding in the removal of foreign bodies, and the like. Essential to the ability of the lymphoid compartment to protect the host against the various pathologies is the ability to recognize self from non-self. In monitoring tumorigenesis, subtle distinctions may be involved and the high incidence of cancer, particularly in the aged, suggests that the monitoring frequently breaks down over time. In addition, because of the enormous diversity of the environment to which the immune system is exposed, there is always the possibility that epitopes will be encountered, which may trigger an immune response which can be directed against self. Other mechanisms may also be operative in the process where a lymphoid cell attacks an endogenous epitope. These autoimmune diseases can be extremely destructive, as is evidenced by diabetes, rheumatoid arthritis, neuronal diseases, such as multiple sclerosis, and the like. While in many cases, the disease is associated with T-cell attack, in some of the diseases, there may be a B-cell component, and in other diseases, such as rheumatoid arthritis and lupus nephritis, the primary mediator may be B-cells.

The lymphoid compartment may be more susceptible than other cells to tumorigenesis, because of the recombinatorial processes associated with the rearrangements involved with formation of immunoglobulins and the T-cell receptor. Lymphoid cancers, such as lymphomas and leukemias are particularly dangerous, because of the opportunity for migration of the lymphoid cells throughout the body and the many sites in the periphery, where lymphocytes reside, so as to provide numerous opportunities for metastasis. Furthermore, these diseases interfere with the native process which is intended to monitor tumorigenesis.

There is, therefore, substantial interest in being able to develop techniques and therapies which will allow for selective reduction in cell types associated with pathogenesis.

Relevant Literature

Grillot-Courvalin et at. (1992) *Eur. J. Immunol.* 22:178 1, describe an anti-B-cell autoantibody from Wiskott-Aldrich syndrome which recognizes i blood group specificity on normal human B-cells. The production of human monoclonal antibodies is described by Bieber and Teng (1987), In vitro sensitization for the production of human monoclonal antibodies, in *Human Hybridomas*, A. J. Strelkauskas ed. Marcel Dekker, Inc., New York, p. 39. Kannagi et at. (1983) *Cancer Res.* 43:4997, describe factors affecting expression of glycolipid tumor antigens. Niemann et al. (1978) *Biochem. Biophys. Res. Comm.* 81:1286, describe Blood group i and I activities of "lacto-N-nor-hexaosylceramide" and its analogues, particularly the structural requirements for i-specificities.

SUMMARY OF THE INVENTION

Methods are provided for inducing cell death in B-cells, including neoplastic B-cells, by employing reagents that bind to a 75 kD glycoprotein B-cell marker. Particularly, antibodies specific for the marker can be administered to a host to induce death in B-cells to which the antibodies bind or can be used in ex vivo clinical situations to selectively remove B-cells.

DESCRIPTION OF SPECIFIC EMBODIMENTS

In accordance with the subject invention, methods and compositions are provided for killing B-cells, particularly neoplastic B-cells, in cellular compositions comprising a plurality of cells, particularly hematopoietic cells. The method allows for a therapy in the treatment of the aberrant proliferation of B-cells and for the selective removal of B-cells from cultures or other ex vivo situations. By B-cells is intended those cells of the B-cell lineage, where B-cells may be defined as comprising surface membrane protein markers found on normal B-cells, such as CD19, CD20, CD21 and CD22.

The CDIM epitope is a three-dimensional structural conformation recognized on normal human, peripheral, and splenic B-cells and on some neoplastic B-cells by the human monoclonal antibody 216. The epitope is defined structurally in terms of spatial conformation, functionally in terms of specific antibody binding, and cytologically in terms of cellular distribution, as described below.

The spatial conformation of CDIM is characterized by being a hexose or longer, straight-chain oligosaccharide comprising acyl-substituted repeating glucosamine subunits. The epitope is structurally related to, but distinct from, the "I" and "i" antigens present on adult and chord red blood cells (RBC's) respectively, and to antigens derived from lipid A, lipooligosaccharides of *N. gonorrhoeae* and *N. meningitides,* and chitin. Structurally related synthetic sugars include gentiobiose octaacetate, trichitose, and lacto-N-norhexosyl ceramide.

The CDIM epitope can be identified on a B-cell surface using fluorescent-labeled human monoclonal antibody (MAb), particularly the human monoclonal antibody 216. Cells carrying the epitope can be analyzed, for example, by a fluorescence-activated cell sorter (FACS). For example, a human MAb can be biotin labeled and detected with fluorescent-labeled streptavidin, where control human MAbs do not bind to the human B-cells.

The CDIM epitope is naturally presented as the glyco-moiety of the glycoprotein known as gp75, an approximately 75 kD MW (as determined by conventional SDS-PAGE) glycoprotein found on substantially all peripheral B-lymphocytes and splenic B-lymphocytes and on certain cultured B-cell lymphoma lines, such as Lam, REH, and JY25. It is also found on 30–40% of primary B-cell lymphomas of various histopathologic classifications. At least about 90% of these various categories of cells, more usually about 100% of these cells, will present the indicated epitope. The antibody 216, which recognizes CDIM on B-cells as described above, does not recognize this epitope on cultured T-cells such as Peer and HUT 78, macrophage lines such as U937, and some B-cell lines such as TAB, Daudi, Ramos, and 8866, since the CDIM epitope is not present on normal T cells, macrophages, NK cells, epithelial, endothelial or mesenchymal cells.

For the purpose of this invention polyvalent (two or more binding sites) CDIM-binding receptors are required. By "receptor" is intended a compound which has a specific affinity for the CDIM epitope, generally at least about $10^{-7}$M, preferably at least about $10^{-8}$M, so as to be able to bind to gp75. The polyvalent nature of the receptor allows the simultaneous binding of at least two gp75 molecules on the cell membrane surface, thereby forming a cross-link. Conveniently, antibodies can be used from any of the immunoglobulin families, such as A, D, E, G, and M; it is not requisite that the antibody be associated with various cytotoxic processes associated with particularly Fc-initiated processes. Usually, the antibody will be IgM, since the pentameric structure of this molecule allows cross-linking unhindered by steric interference. Binding of at least two gp75 molecules on the same cell surface by the same receptor elicits a cellular response, resulting ultimately in cell death. Besides antibodies, other receptors with the indicated affinity will find use, where the receptor can, for example, be associated with a lectin either naturally occurring or modified. Alternatively, small synthetic molecules can be devised which will allow for specific binding and cross linking of the CDIM epitope. One may subject the variable region of a MAb to mutagenesis to enhance the binding affinity of an antibody for the CDIM epitope, if desired.

The gp75- and CDIM-binding agents can be used in therapy for treatment of B-cell proliferative diseases, such as B-cell neoplasia and autoimmune diseases. Thus, the subject agents will find application in the treatment of autoimmune-mediated disease, particularly B-cell-mediated disease. For example, the human MAb 216, by binding to at least two CDIM epitopes on the same cell, causes the death of the cell expressing this epitope. Epitope-mediated death does not require complement or cell-mediated lysis. While, for the most part, human cells in human patients will be a primary interest, other animals, particularly domestic animals, will also be served by the subject methodology to the extent that a given agent reacts across species, which is readily determined by binding studies of the type described herein.

For therapeutic uses, the compositions and selective agents disclosed herein can be administered by any convenient technique, which can vary depending on the nature of the compound/agent, the purpose and frequency of the treatment, and the like. For small molecular weight agents, oral administration is preferred, and enteric coatings are indicated where the compound is not expected to retain activity after exposure to the stomach environment. Generally the amount administered will be empirically determined, typically in the range of about 0.1 to 1000 $\mu$g active ingredient per kg of recipient, with adjustment by a physician or other person after consideration of clinical results.

Large proteins are preferably administered parenterally or systemically, conveniently in a physiologically acceptable carrier, e.g., phosphate buffered saline, saline, or deionized water. Some agents such as antibodies can also be administered nasally. Typically, compositions are administered to a retained physiological fluid such as blood. Other additives can be included, such as stabilizers, or bacteriocides. These additives, if present, will be present in conventional amounts.

The subject agents can also be used for treating cell populations in culture to diminish the B-cell population, whether normal or neoplastic, in the culture. Thus, in mixed cultures, where one wishes to avoid interference by B-cells, where one is interested in studying antigen-presenting-cell mechanisms other than those associated with B-cells, where one is analyzing for cells associated with mediating secretion of a particular cytokine, or where one wishes to study a mixed cell population for other purposes without the presence of B-cells, this can be achieved by adding an amount of the subject agent effective to remove substantially all of the B-cells present in the culture. In a similar manner ex vivo therapeutic treatments can be utilized in which blood is removed from a patient into an external environment (as in dialysis), treated to remove excess B-cells, and then returned to the patient.

Where CDIM epitope-specific antibodies are administered therapeutically, it is desirable to minimize the likelihood of an immunogenic or allergenic response by using host-specific antibodies (e.g., human antibodies in humans). While intact antibodies are commonly used, the antibodies may be modified in a variety of ways, by enzymatic cleavage to provide fragments, reduction of disulfide linkages, and the like.

In referring to an isolated component or compound, the isolated component or compound will constitute at least about 1%, usually at least about 10%, and more usually at least about 50% by weight of the isolated material. By pure compound or composition is intended at least about 90%, usually at least 95%, and more usually at least about 99% by weight of the component or compound. Unless otherwise indicated, functional fragments will also be intended when referring to components or compounds.

The following examples are offered by way of illustration and not by way of limitation.

EXAMPLES

Production, characterization, and conjugation of human MAbs.

Human MAb 216 was prepared by diffusion of uninvolved spleen lymphocytes from a patient with nodular lymphoma. The cells were incubated in vitro with LPS and fused to the heteromyeloma line SHMD33. This antibody was found to be mu, lambda using peroxidase-labeled chain-specific antibodies (Cal Tag, South San Francisco, Calif.). Nucleotide analysis of the heavy chain showed it was encoded by the VH 4.21 gene.

Human MAbs were purified on high pressure liquid chromatography using a carboxymethyl column (BioRad, Richmond, Calif.). Hybridoma supernatant containing 1% FCS was diluted 1:4 with 20 mM Na acetate pH 5.5 The MAbs were eluted with 300 mM NaCl Tris buffer pH 8, dialyzed in PBS and concentrated if necessary on a Centriprep concentrator (Areicon, Danvers, Mass.). By PAGE analysis the purified material was 85–90% IgM and also contained transferrin and BSA. Concentration of the purified immunoglobulins was determined by sandwich ELISA using a human polyclonal IgM standard (Cooper Biomedical, Malvern, Pa.).

MAb 216 and other human IgM MAbs were biotinylated using N-hydroxysuccinimidobiotin (Pierce, Rockford, Ill.) at a ratio of 60 $\mu$g/mg IgM.

Flow cytometry

Human adult splenic mononuclear cells were obtained from patients undergoing therapeutic splenectomy, and peripheral blood was obtained from normal volunteers. Lymphoma cells were obtained by biopsy or laparotomy for removal of tumor. All procedures had the approval of the Committee for the Protection of Human Subjects at Stanford University. Spleens were gently teased apart in HBSS with 1% FCS and 0.2% DNase and passed through sterile nylon membranes to obtain single-cell suspensions. Peripheral blood and splenocytes were centrifuged at 800 g for 30 min through a ficol/hypaque gradient (Histopaque-1077, Sigma, St. Louis, Mo.). The mononuclear cell population was washed three times in HBSS with 1% FCS and resuspended in staining medium (RPMI with 3% FCS, 1 mM EDTA, and 0.01M HEPES)at $2.5 \times 10^7$ cells/ml.

Tumor tissue that had been removed from patients at surgery was disassociated into a cell suspension and frozen in DMSO with storage in liquid nitrogen. The cells were thawed and incubated overnight at 37 degrees before staining. The thawed cells were also incubated 24 hours with human MAb 216 or control human IgM MAbs and stained with propidium iodide (PI) which measures cell death.

Multi-parameter flow cytometric analysis (FACS) has been described in detail (Parks et at. (1986) *The Handbook of Experimental Immunology*, supra, p. 29). Fluorescent-labeled mouse MAbs against CD epitopes were from Becton Dickinson. $5 \times 10^5$ cells were suspended with predetermined saturating concentrations of each of the conjugated fluorescent antibodies in a final volume of 125 µl, and incubated on ice for 15 min. The cells were washed and resuspended in 200 µl of staining medium and analyzed on a highly modified dual-laser FACS II (*Becton Dickinson*, Mountain View, Calif.), interfaced with a VAX 6300 computer (Digital Equipment, Maynard, Mass.) running FAGS/desk software (Moore and Kautz (1986) *The Handbook of Experimental Immunology*. supra p. 30). Dead cells are identified with the propidium iodide (1 µg/ml) signal collected in the APC- or TR-channel in experiments with three-colors (Parks et at. (1986) supra).

Endo-β-galactosidase treatment of cells

Peripheral blood B lymphocytes were incubated at 37° C. for one hour at $5 \times 10^6$ cells/ml in Iscove's with 5% FCS, with 15 mU/ml of endo-β-galactosidase (Boehringer Mannheim, Indianapolis, Ind.). The cells were washed and stained for FACS analysis. Cord RBCs at 50% concentration were incubated with 0.1 U/ml of endo-β-galactosidase at 37° C. for 4 hours, washed and tested for hemagglutination.

RESULTS

216 MAb reacts with a carbohydrate ligand on human splenic and peripheral B lymphocytes.

Multiparameter FACS analysis of human mononuclear cells demonstrated that the MAb binds specifically to all B lymphocytes (CD20+) obtained from human spleen and adult peripheral blood. MS2B6, a human monoclonal IgM used as an isotype control, did not bind human B lymphocytes, nor did other polyreactive natural antibodies.

The B lymphocytes reacting with 216 were also positive for other pan-B cell markers, such as CD19, CD21, and CD22. Excess amount (10X) of antibodies to CD19, CD20, CD21, CD22, and IgM did not inhibit the binding of 216 to B cells. 216 does not distinguish between subsets of B lymphocytes, reacting with both CD5+ and CD5− B cells. The MAb also did not distinguish between the isotype expressed, reacting with both surface IgG or IgM bearing B lymphocytes.

Mononuclear cells from human peripheral blood were treated with endo-β-galactosidase, and then stained with MAb 216. Reactivity to human B lymphocytes is significantly reduced in enzyme-treated cells. Expression of an unrelated B cell marker (CD19) does not change following enzyme treatment. Thus, sensitivity of both B lymphocytes and cord RBC to endo-β-galactosidase treatment, suggests that the epitope recognized by the two antibody on B lymphocytes is also a carbohydrate antigen similar to the linear polylactosamine structure of the "i" antigen.

216 MAb binds to lymphoma cells

Twenty-seven primary lymphomas were analyzed by FACS. Twenty-three were B-cell lymphomas. The MAb 216 did not react with any T-cell lymphomas and stained 10 of 23 B-cell lymphoma. The MAb 216 did not stain any small cleaved cell (follicular) lymphoma. The MAb 216 stained the following classes of lymphoma; immunoblastic, diffuse large well differentiated, diffuse large cell, diffuse mixed, and diffuse small cell.

In vitro B-cell toxicity of 216

Human MAb 216 is incubated in vitro at an Ab concentration of 10–20 µl/ml with various types of cells. The cells are in tissue culture media with heat-inactivated normal human serum or in serum-free media and are incubated at 37° C. in 5% $CO_2$. After 18–24 hours incubation the cells are stained with propidium iodide (PI) and/or Hoechst dye 33242 (and other Ab for determining type of cell) and analyzed on FACS. Cell death is determined by uptake of PI and decreased DNA staining with Hoechst dye. When human spleen or peripheral blood lymphocytes are incubated with MAb 216, 60–80% of B cells are killed. Four primary lymphoma cell suspensions that stained with the MAb 216, and two that did not, were incubated 24 hours with either 20 µl/ml of the 216 MAb or control human MAb in medial at 37 degrees in 5% $CO_2$. The cells were analyzed for cell death using propidium iodide (PI) on FACS. The lymphoma cell suspensions that bound the MAb 216 showed significant PI uptake compared to the control MAb. The two lymphoma cell suspensions that did not bind MAb 216 did not take up PI. When B cell lymphoma lines are incubated with MAb 216, 60–80% of the cells are killed. MAb 216 does not kill T cells, NK cells or monocytes. Other control human MAbs cause 0–5% cell death under the same conditions.

Isolation and Characterization of gp75

Isolation

The B cell membrane proteins and glycoproteins including gp75 can be extracted and solubilized using a non-ionic detergent (such as Triton X). The B-cell membrane protein solution is passed over a column to which the MAb 216 has been covalently bound using N-hydroxy succinimide coupled to acrylamide beads (Affi Gel). The CDIM epitope is bound to the 216 MAb and the gp75 is removed from the membrane solution. The column is washed to remove other proteins. The gp75 can be released from the column by competition with lacto-N-nor-hexosylceramide contained in liposomes which will competitive bind to the MAb 216.

Characterization of CDIM Ag

The MAb 216 binds to synthetic I/i antigen.

The following glycolipids were run on TLC: i antigen (lacto-N-norhexaosylceramide), sialyl i antigen, paraglobolside (lacto-N-tetraocylceramide), sialyl paragloboside, I antigen (branched), and GM3. The MAb 216 was applied to the plate. The plate was washed and $I^{125}$—labeled goat anti-human IgM was applied to the plate, washed and incubated with X ray film. The TLC plate was then sprayed with sulfuric acid and heated to visualize the glycolipids. Comparing the TLC plate and exposed film revealed that 216 bound i antigen, sialyl i antigen, I antigen, and sialyl I antigen only. i Antigen (Lacto-N-nor-hexaosylceramide): Gal$\beta$ 1–4 GIcNAc$\beta$ 1–3 Gal$\beta$ 1–4 GIcNAc$\beta$ 1–3 Gal$\beta$ 1–4 Glc$\beta$ 1-Ceramide. Sialyl I Antigen: NeuAc$\alpha$ 2–3 Gal$\beta$ 1–4 GIC-NAc$\beta$ 1–3 Gal$\beta$ 1–4 GLcNAc$\beta$ 1–3 Gal$\beta$ 1–4 Glc$\beta$ 1-Ceramide. Paragloboside (Lacto-N-tetraocylceramide): Gal$\beta$ 1–4 GIcNAc$\beta$ 1–3 Gal$\beta$ 1–4 Glc$\beta$ 1-Ceramide. Sialyl Paragloboside: NeuAc $\alpha$ 2–3 Gal$\beta$ 1–4 GIcNAc$\beta$ 1–3 Gal$\beta$ 1–4 Glc$\beta$ 1- Ceramide. GM3: NeuAc $\alpha$ 2–3 Gal$\beta$ 1–4 Glc$\beta$ 1-Ceramide.

SUMMARY 216 binds all CD19+ and CD20+ B lymphocytes in human peripheral blood and spleen. Furthermore, 216 does not distinguish B cells by the isotype expressed, binding IgG+ and IgM+ cells with equal intensity, and also bind all B cells regardless of their CD5 expression. Accordingly, the ligand being recognized on B lymphocytes is a novel glycoprotein, with no apparent similarities to any of the known pan-B cells markers.

It is evident from the above results and disclosure that a novel B-cell marker and a specific oligosaccharide epitope thereof have been identified. In addition, novel proteins which specifically bind the disclosed epitope are provided. These products and products derivable therefrom find use in diagnosis and therapy. A deposit of the hybridoma cell line secreting mAb 216 was made with the ATCC in Rockville, Md. USA, as Deposit No. HB 11659, on Jun. 14, 1994.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for killing B-cells within a mixed population of cells, said method comprising:
    contacting said mixed population of cells with an antibody/carrier compostion in which the active ingredient consists of a cytotoxic amount of a monoclonal antibody that specifically binds CDIM, wherein the killing of B-cells occurs in a complement-independent and cell-mediated independent manner, and wherein the said mixed population of cells is outside a mammalian host.

2. The method of claim 1, wherein said monoclonal antibody is an IgM.

3. The method of claim 1, wherein said B-cells are neoplastic.

4. The method of claim 1, wherein said mixed population of cells is hematopoietic.

5. The method according to claim 1, wherein said B-cells mediate an autoimmune disease.

6. The method of claim 2, wherein the monoclonal antibody is the monoclonal antibody produced by the hybridoma cell line ATCC HB 11659.

7. The method of claim 1, wherein the monoclonal antibody is a human monoclonal antibody.

* * * * *

UNITED STATES PATENT AND TRADEMARK OFFICE
CERTIFICATE OF CORRECTION

Page 1 of 2

PATENT NO. : 5,417,972
DATED : May 23, 1995
INVENTOR(S) : Neelima M. Bhat, et. al.

It is certified that error appears in the above-indentified patent and that said Letters Patent is hereby corrected as shown below:

In column 2, line 7, delete "75 kD glycoprotein".

In column 2, lines 53-57, please make the following deletion. After "epitope is" on line 53, begin deletion with "naturally presented" and continue deletion through "glycoprotein" on line 56. Thus, the sentence of lines 53-57 should read: "The CDIM epitope is found on substantially all peripheral..."

In column 3, lines 7-8, after "$10^8 M$" on line 7, delete ", so as to be able to bind to gp75".

In column 3, line 10 and line 19 (two occurrences), after "at least two", delete "gp75 molecules" and insert in place thereof --CDIM epitopes--.

In column 3, line 30, delete "gp75- and".

UNITED STATES PATENT AND TRADEMARK OFFICE
CERTIFICATE OF CORRECTION

PATENT NO. : 5,417,972
DATED : May 23, 1995
INVENTOR(S) : Neelima M. Bhat, et. al.

It is certified that error appears in the above-indentified patent and that said Letters Patent is hereby corrected as shown below:

In column 6, delete lines 47, 48, and paragraph beginning with "The B cell membrane proteins" at line 49. Continue deletion through "MAb 216." at line 60 of column 6.

In column 7, line 24, after "B lymphocytes" delete "is a novel glycoprotein, with". Substitute in place thereof --has--.

Signed and Sealed this

Ninth Day of April, 1996

Attest:

BRUCE LEHMAN

*Attesting Officer*    Commissioner of Patents and Trademarks